US011117182B2

(12) United States Patent
Durand

(10) Patent No.: US 11,117,182 B2
(45) Date of Patent: Sep. 14, 2021

(54) METHODS FOR FABRICATION OF AN ELECTRODE DELIVERY SYSTEM

(71) Applicant: Case Western Reserve University, Cleveland, OH (US)

(72) Inventor: Dominique Durand, Solon, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 466 days.

(21) Appl. No.: 15/776,151

(22) PCT Filed: Nov. 18, 2016

(86) PCT No.: PCT/US2016/062758
§ 371 (c)(1),
(2) Date: May 15, 2018

(87) PCT Pub. No.: WO2017/087793
PCT Pub. Date: May 26, 2017

(65) Prior Publication Data
US 2020/0254507 A1    Aug. 13, 2020

Related U.S. Application Data

(60) Provisional application No. 62/256,781, filed on Nov. 18, 2015, provisional application No. 62/328,835, filed on Apr. 28, 2016.

(51) Int. Cl.
*B21F 9/00* (2006.01)
*A61B 5/00* (2006.01)
(Continued)

(52) U.S. Cl.
CPC ............... *B21F 9/002* (2013.01); *A61B 5/24* (2021.01); *A61B 5/6868* (2013.01);
(Continued)

(58) Field of Classification Search
CPC .......... A61B 2562/125; A61B 5/04001; A61B 5/6868; A61N 1/0534; A61N 1/0551; B21F 9/002
See application file for complete search history.

(56) References Cited

U.S. PATENT DOCUMENTS 7,949,408 B2 *  5/2011  Bonde .................. A61N 1/0551
                                                     607/116
2015/0141786 A1   5/2015  Durand et al.
(Continued)

FOREIGN PATENT DOCUMENTS

WO    2015/157393 A2    10/2015

OTHER PUBLICATIONS

PCT International Search Report and Written Opinion for corresponding Application Serial No. PCT/US2016/062758, dated Mar. 1, 2017, pp. 1-13.

*Primary Examiner* — Minh N Trinh
(74) *Attorney, Agent, or Firm* — Tarolli, Sundheim, Covell & Tummino LLP

(57) ABSTRACT

A method for fabricating electrodes sized and dimensioned to record, measure, and/or stimulate very fine nerve structures (e.g., microscale or less) is described herein. The method can include securing a tip of an electrode, comprising a conductor substantially encased by an insulator, to a proximal portion of an inserter. The electrode can be wound around a proximal portion of the inserter and a portion of the electrode can be secured to a distal portion of the inserter. A tension in the electrode can be maintained during the winding to keep the electrode in place during the winding.

12 Claims, 5 Drawing Sheets

(51) Int. Cl.
*A61N 1/05* (2006.01)
*A61B 5/24* (2021.01)
(52) U.S. Cl.
CPC ......... *A61N 1/0534* (2013.01); *A61N 1/0551* (2013.01); *A61B 2562/125* (2013.01)

(56) References Cited

U.S. PATENT DOCUMENTS

| | | | |
|---|---|---|---|
| 2016/0158533 A1* | 6/2016 | Jolly | A61N 1/0541 600/377 |
| 2018/0264255 A1* | 9/2018 | Durand | A61N 1/0558 |
| 2020/0254507 A1* | 8/2020 | Durand | A61B 5/6868 |

\* cited by examiner

METHODS FOR FABRICATION OF AN ELECTRODE DELIVERY SYSTEM

RELATED APPLICATIONS

This application claims the benefit of U.S. Provisional Application No. 62/328,835, entitled "METHODS FOR FABRICATION OF AN ELECTRODE DELIVERY SYSTEM," filed Apr. 28, 2016. This application also claims the benefit of U.S. Provisional Application No. 62/256,781, entitled "NANOWIRE INTERFACE FABRICATION", filed Nov. 18, 2015. The entirety of these provisional applications is hereby incorporated by reference for all purposes.

TECHNICAL FIELD

The present disclosure relates generally to fabrication of an electrode delivery system, and, more specifically, to methods for fabricating a delivery system for electrodes sized and dimensioned to record, measure, and/or stimulate nerve structures.

BACKGROUND

Electrodes that can be used for recording, measuring, and/or stimulating very fine neural structures have attracted much interest. One example of such an electrode can be sized and dimensioned (e.g., microscale or smaller) for insertion into a fascicle for intra-fascicular recording, measuring, and/or stimulating. Another example of such an electrode can be sized and dimensioned (e.g., microscale or smaller) for insertion into the brain for deep brain stimulation, measuring, and/or recording. However, there exists no method that can efficiently and reliably fabricate a delivery system for these electrodes.

SUMMARY

The present disclosure relates generally to fabrication of an electrode delivery system, and, more specifically, to methods for fabricating a delivery system for electrodes sized and dimensioned to record, measure, and/or stimulate nerve structures. In some examples, the nerve structures can be very fine, so the electrodes can be sized and dimensioned on with a diameter of 100 µm or less and an unconstrained length.

In one aspect, the present disclosure can include a method for fabricating a delivery system for an electrode capable of recording, measuring, and/or stimulating very fine nerve structures. The method includes securing a tip of an electrode (including a conductor substantially encased in an insulator) to a proximal portion of an inserter; winding the electrode around a proximal portion of the inserter; and securing a portion of the electrode to a distal portion of the inserter. During the winding, a tension in the electrode is maintained to keep the electrode in place during the winding.

In another aspect, the present disclosure can include a method for fabricating a delivery system for a multiple channel interface that can be used for recording, measuring, and stimulating very fine nerve structures. The method includes securing a tip of a first electrode to a proximal portion of an inserter; securing a tip of a second electrode to a more distal portion of the inserter; winding the first electrode and the second electrode around the inserter; and securing portions of each of the first electrode and the second electrode to a distal portion of the inserter.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
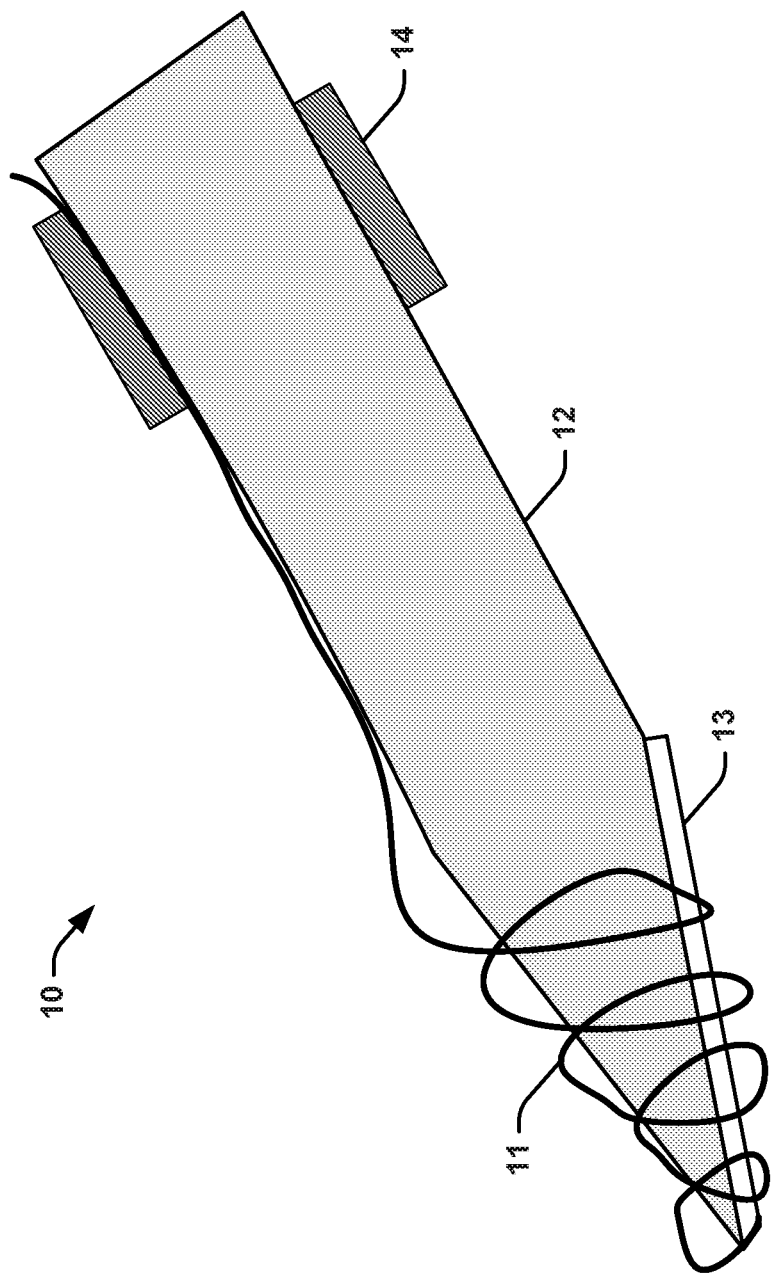
FIG. 1 is a block diagram showing an example of an assembled electrode delivery system.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "delivery system" can refer to one or more devices that facilitate delivery of an electrode to a location in a patient's body. In some instances, the location in the patient's body can be on, in, or near a nerve. For example, the delivery system can include at least an inserter and an electrode.

As used herein, the term "inserter" can refer to a generally cylindrical device that includes at least a portion shaped and dimensioned to wind, turn, or knot the electrode therearound. In some instances, the inserter can have a sharp edge or tip to facilitate delivery of the electrode to a location in the patient's body. In some instances, a device (e.g., like an array, such as a Utah-type array) can include a plurality of inserters.

As used herein, the term "electrode" can refer to a conductor through which a current enters or leaves a non-metallic medium. In some instances, the conductor can be substantially encased in an insulator with one or more contacts exposed to deliver or receive the current to the non-metallic medium.

As used herein, the term "wire" can refer to a conductor (metallic or non-metallic) sized and dimensioned on the microscale or less. In other words, the wire can have an unconstrained longitudinal size (or length) and a lateral size (or diameter) constrained as 100 μm or less. In some instances, the lateral size can be constrained to 10 μm or less. In other instances, the lateral size can be constrained to 1 μm or less. In still other instances, the lateral size can be constrained to 0.1 μm or less. In further instances, the lateral size can be constrained to 0.01 μm or less. In still further instances, the lateral size can be constrained to 0.001 μm or less.

As used herein, the term "insulator" can refer to a material with internal electric charges that do not flow freely, making it nearly impossible to conduct an electric current under the influence of an electric field. In other words, an insulator can be generally non-conductive.

As used herein, the term "contact" can refer to a conductive area of an electrode. For example, a contact can be an area of the conductor not covered by the insulator.

As used herein, the conductor being "substantially" encased in the insulator can refer to the entire conductor being encased in the insulator but for one or more contacts. In other words, the wire can be about 98%, about 95%, about 93%, about 90%, about 80%, about 70%, or about 50% or less encased by the insulator.

As used herein, the term "nerve" can refer a cell that employs electrical and chemical signals to transmit information. Although the term nerve is generally used in reference to the peripheral nervous system, a nerve can also refer to a component of the central nervous system.

As used herein, the term "peripheral nervous system" can refer to a part of the nervous system that consists of the nerves and ganglia outside the brain or spinal cord. The peripheral nervous system can include motor, sensory, and/or autonomic fibers. One or more such fibers can be included in a fascicle to transmit information from one body part to another. For example, a nerve can include one or more fascicles, each fascicle including one or more fibers (or "nerve structures").

As used herein, the term "central nervous system" can refer to the brain and spinal cord. As an example, a nerve can be a component of the brain and/or the spinal cord.

As used herein, the term "automated" can refer to a process that functions automatically without continuous human intervention.

As used herein, the term "proximal" can refer to an area close to a center position. In some instances, the center position can be a point where the electrode contacts the inserter. For example, the center position can be at or near the sharp tip of the inserter.

As used herein, the term "distal" can refer to an area distant from the center position. The terms proximal and distal refer to directions that are opposites.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to fabrication of an electrode delivery system. In some instances, the electrodes delivered into a patient's body using the delivery system can be sized and dimensioned to record, measure, and/or stimulate very fine nerve structures (e.g., on the microscale or smaller). For example, the electrode can be used in the peripheral nervous system for intra-fascicular applications. In another example, the electrode can create an interface with the central nervous system for deep brain stimulation. Advantageously, the methods described herein provide an entirely (or at least partially) automated process that ensures the efficient, reproducible, and reliable fabrication of uniform electrode delivery systems.

III. Systems

One aspect of the present disclosure can include a fabrication system 20 (FIG. 2) for an electrode delivery system 10 (FIG. 1). In some instances, the fabrication system 20 can be entirely (or at least partially) automated to ensure uniform fabrication of electrode delivery system 10. The fabrication system 20 can ensure that the structure and configuration of the electrode delivery system 10 is highly reproducible. Advantageously, the fabrication system 20 can ensure efficient and reliable fabrication of multiple electrode delivery systems 10.

The electrode delivery system 10 includes at least an electrode 11 and an inserter 12. An example of the structure and function of such an electrode delivery system 10 is shown and described in more detail in International Patent Application PCT/US2015/024855, entitled "Neural Electrodes and Methods for Implanting Same" by Durand, et al., which is hereby incorporated by reference in its entirety.

In some instances, the electrode 11 can include a conductive wire substantially encased in an insulator. The conductive wire can have an unconstrained longitudinal (length) size and a lateral (diameter) sized and dimensioned on the microscale or less. In some instances, the diameter size can reduce or eliminate damage to a nerve while minimizing an immune response to the electrode 11. The conductive wire can have a cross-sectional profile that is circular, oval, square, rectangular, or the like. The cross-sectional profile and/or the diameter of the conductive wire can vary depending on a particular application for the electrode 11. Additionally, the conductive wire can be made of one or more materials capable of conducting a current therethrough. The one or more materials can be metallic or non-metallic. Examples of such materials can include platinum, iridium, gold, silver, carbon, combinations, oxides, or the like.

The insulator can include one or more insulating materials that generally do not permit transmission of charge. In some examples, the insulating material can be one of parylene, silicone, or plasma-deposited amorphous carbon. In one example, the insulating material can comprise a 2 micron layer of plasma-modified silicone. At least one biocompatible agent can be adsorbed to an outer surface of the insulating material. The biocompatible agent can include any biological or organic molecule that improves the biocompatibility of the electrode 11.

The inserter 12 can have a generally cylindrical shape including a sharp portion to facilitate entry through tissue. In some instances, the sharp portion can be the tip of the inserter 12. For example, the inserter 12 can be a needle. The electrode 11 can be wrapped, wound, and/or coiled around a portion of the inserter. In some instances, the portion of the inserter can be a proximal portion of the inserter at or close to the tip (e.g., less than 10 mm, less than 20 mm, less than 30 mm, less than 40 mm, etc.).

The electrode 11 can be coupled to the inserter 12 so that a small tension is applied in the proximal region of the inserter to maintain the electrode in place. For example, at least a portion of the electrode 11 can be releaseably coupled to the inserter 12 via a selective release mechanism 13, which can establish the required tension. In some instances, at least a tip of the electrode 11 can be coupled to the inserter 12 by the selective release mechanism 13. The selective release mechanism 13 can enable the electrode 11 to be temporarily attached to the inserter 12 (e.g., so that the electrode 11 is attached during implantation of the electrode into a patient's body (e.g., into a fascicle of a peripheral nerve or into a portion of the central nervous system), but released after implantation). In some examples, the selective release mechanism 13 can include one or more biocompatible and biodegradable elements (e.g., including a type of sugar, like sucrose). However, the selective release mechanism 13 is not limited to being biodegradable and can, instead, release based on tactile, chemical, mechanical, electrical, and/or optical means.

In some instances, a distal portion of the electrode 11 can be secured to a distal portion of the inserter 12 by a holding mechanism 14. The holding mechanism 14 can include one or more of an adhesive material, an adhesive tape, or a knot in the electrode 11.

Figure 2:
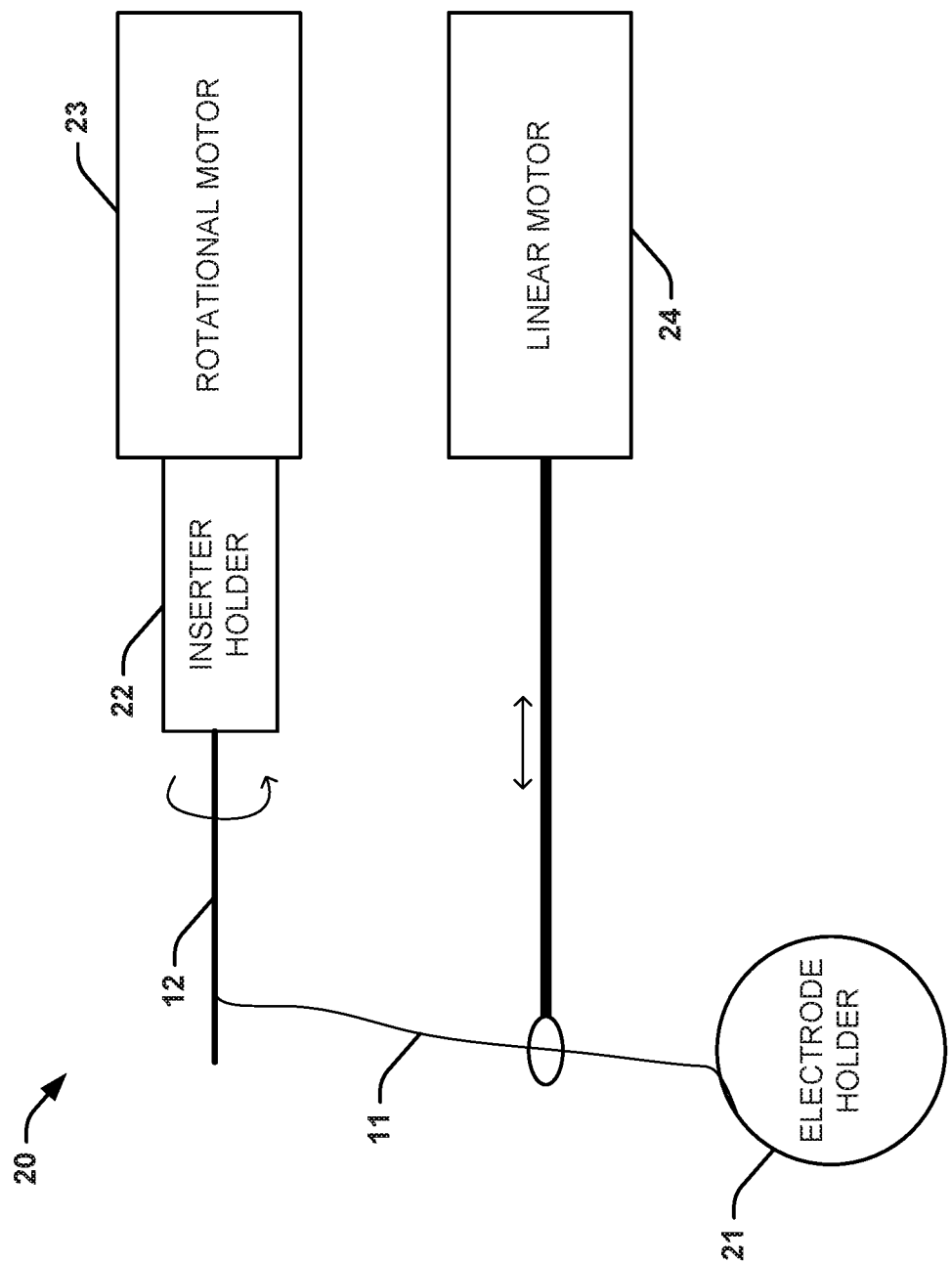
FIG. 2 is a block diagram showing an example of a fabrication system that can be used to assemble the example electrode delivery system shown in FIG. 1, according to an aspect of the present disclosure.

The electrode delivery system 10 can be fabricated in an at least partially automated fashion by an electrode fabrication system 20, as shown in FIG. 2. The electrode fabrication system 20 can include an inserter holding mechanism 22 to secure the inserter 12 in place. The electrode 11 can be attached to or wrapped around a holder 21 (e.g., a spool, frame, or other mechanism). A free tip of the electrode 11 can be positioned on the inserter 12. For example, the free tip of the electrode 11 can be positioned at or near the proximal tip of the inserter 12. The free tip of the electrode 11 can be secured to this position by the selective release mechanism 13. A small tension can be maintained in the electrode by the attached holder 21.

The electrode fabrication system 20 can include at least two motors 23, 24. For example, the electrode fabrication system 20 can include a rotational motor 23 to rotate the inserter 12 to initiate the winding of the electrode 11 around the inserter 12. The electrode fabrication system 20 can also include a linear motor 24 to move (or translate) the electrode 11 along the shaft of the inserter 12 to produce several turns or coils. Accordingly, after the free tip of the electrode 11 is secured to the inserter 12 by the selective release mechanism 13, the electrode 11 can be rotated by one motor (rotational motor 23) and simultaneously moved linearly by the other motor (linear motor 24) to initiate the winding of the electrode, thereby producing several turns or coils in the electrode 11. In other instances, the electrode 11 can be knotted around the inserter 12 using a knot (e.g., a cleat hitch knot) that can be undone by releasing the pressure on the electrode.

After a predefined number of turns or coils are established, a distal end of the electrode 11 can be secured to the distal shaft of the inserter 12 by a holding mechanism 14 (e.g., an adhesive, tape, a knot, etc.). In some instances, the electrode 11 can be cut or otherwise separated from the spool, frame, or other mechanism either before or after being secured by the holding mechanism 14. Upon completion, the electrode delivery system 10 can be removed from the electrode fabrication system and placed into a carrier to isolate the electrode 11 from mechanical interference.

In some instances, a multiple channel interface can be achieved by winding several electrodes 11 around the inserter 12 at the same time. The several electrodes can be wound around the same inserter 12 simultaneously by adding at least one additional motor for translation of the additional electrode to the electrode fabrication system. The several electrodes 11 can be made of the same materials or different materials.

Figure 3:
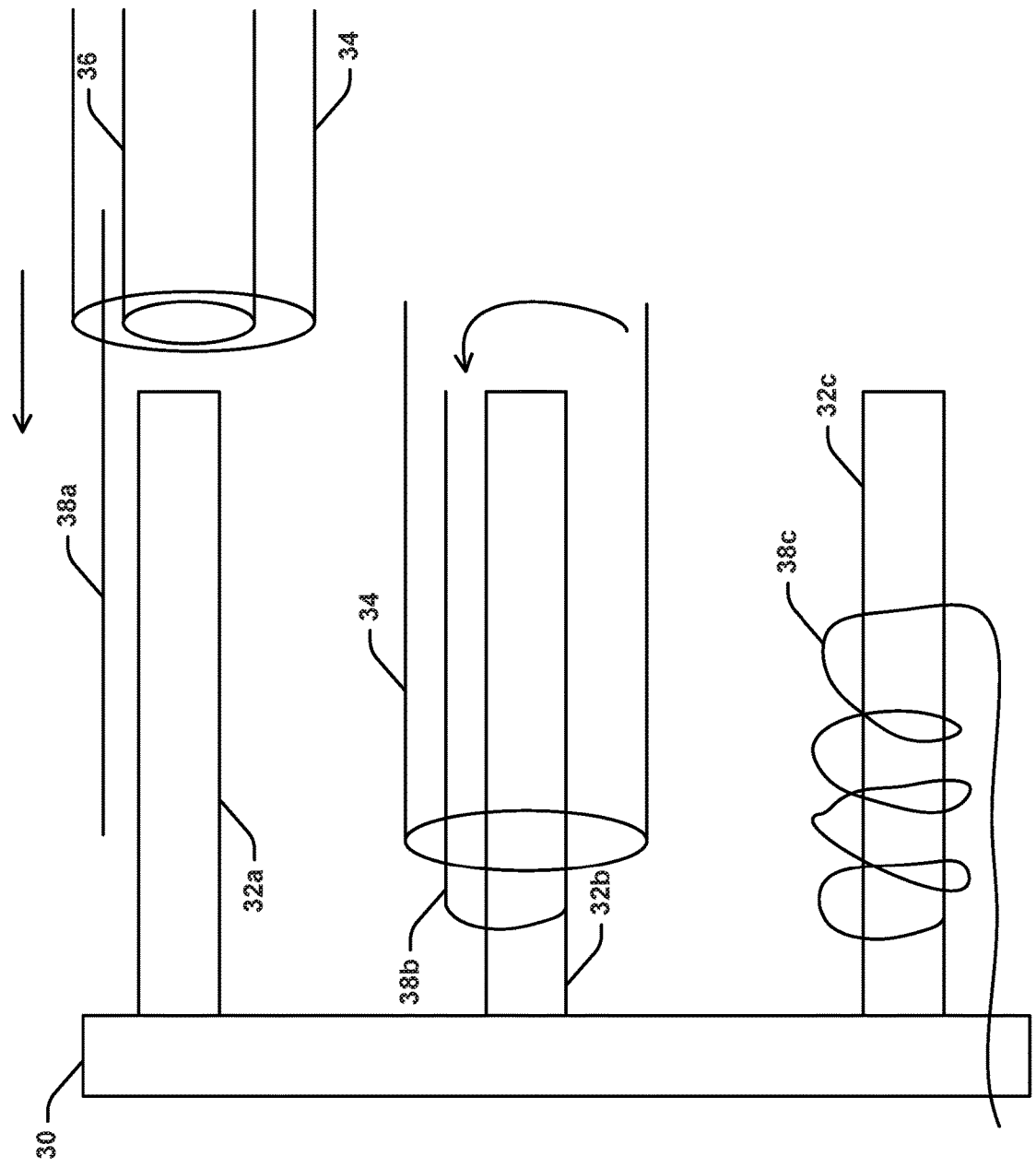
FIG. 3 is a block diagram showing another example of a fabrication system that can be used to assemble a plurality of the example electrode delivery system shown in FIG. 1, according to another aspect of the present disclosure.

As another example, shown in FIG. 3, a microelectrode array 30, such as a Utah-type array, can be constructed as an inserter. The microelectrode array 30 can have a plurality of tips 38 *a-c* that can serve as inserters. Although the microelectrode array 30 is shown with three tips 32 *a-c*, it will be understood that the microelectrode array 30 can have any number of tips greater than or equal to three. Each of the plurality of tips 32 *a-c* can have an electrode 38 *a-c* wrapped therearound, and each of the plurality of tips 32 *a-c* can act as an inserter for the respective electrode 38 *a-c*.

FIG. 3 shows three electrodes 38 *a-c* in different stages of fabrication. However, the fabrication process can be completed sequentially, as shown in FIG. 3, or together so any portion of the electrodes 38 *a-c* (including all) are constructed simultaneously. The electrodes 38 *a-c* can be wrapped, wound, and/or coiled around a portion of the tips 32 *a-c* by a winding tool 34. The winding tool 34 can be at least partially hollow so that the winding tool 34 fits around and over the tip and the electrode. In some instances, the winding tool 34 can have an inserter 34 therewithin.

The winding tool 34 can advance along the electrode 38*a* and onto the respective tip 32*a*. In some instances, the electrode 38*a* can be completely within the winding tool 34. The end of the electrode 38*b* can be attached to the tip, in some instances, by a selective release mechanism, which can include one or more biocompatible and biodegradable elements (e.g., including a type of sugar, like sucrose). However, the selective release mechanism is not limited to being biodegradable and can, instead, release based on tactile, chemical, mechanical, electrical, and/or optical means. The winding tool 34 can wind the electrode 38*b* around the tip 32*b* to facilitate the creation of a wound or otherwise shaped electrode 38*c*. In some instances, however, the winding tool 34 does not move and, instead, the array 30 can move to facilitate the creation of the wound or otherwise shaped electrode 38*c*.

For example, the microelectrode array 30 can be used to deliver the wound or otherwise shaped electrode 38 *c* (as well as other similarly wound or otherwise shaped electrodes) into the brain or to one or more peripheral nerves. The microelectrode array 30 can be removed after the wound or otherwise shaped electrode 38 *c*, is positioned in the brain or the one or more peripheral nerves.

IV. Methods

Another aspect of the present disclosure can include a method 40 (FIG. 4) for fabricating an electrode delivery system 10. In some instances, the method 40 can be performed by fabrication system 20 or microelectrode array 30. The method 40 can be at least partially automated to minimize human interaction and maximize reproducibility. Methods 50-70 (FIGS. 5-7) show the steps of method 40 in greater detail. The methods 40-70 are illustrated as process flow diagrams with flowchart illustrations. For purposes of simplicity, the methods 40-70 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40-70.

Figure 4:
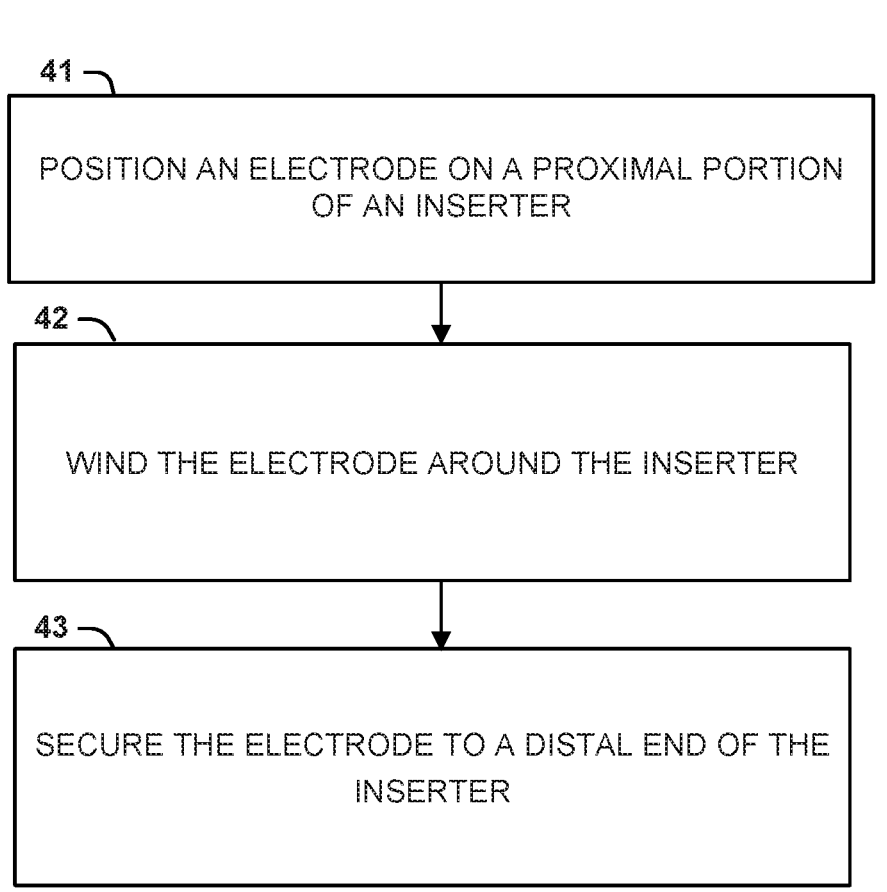
FIG. 4 is a process flow diagram of an example method for fabricating an electrode delivery system, according to another aspect of the present disclosure.

Referring now to FIG. 4, the method 40 fabricates the electrode delivery system 10 in an at least partially automated fashion. At 41, an electrode 11 can be positioned on or near a proximal portion of an inserter 12. For example, a tip of the electrode 11 can be positioned on the proximal portion of the inserter 12. At 42, the electrode 11 can be wound around the inserter 12. In some instances, instead of winding, the electrode 11 can be tied in a knot around the inserter 12. At 43, the electrode 11 can be secured (e.g., by a holding mechanism 14, such as an adhesive, tape, a knot, or the like) to a distal end of the inserter 12. Upon completion of the method 30, the completed electrode delivery system 10 can be removed from the electrode fabrication system 20 and placed into a carrier to isolate the electrode 11 from mechanical interference.

Figure 5:
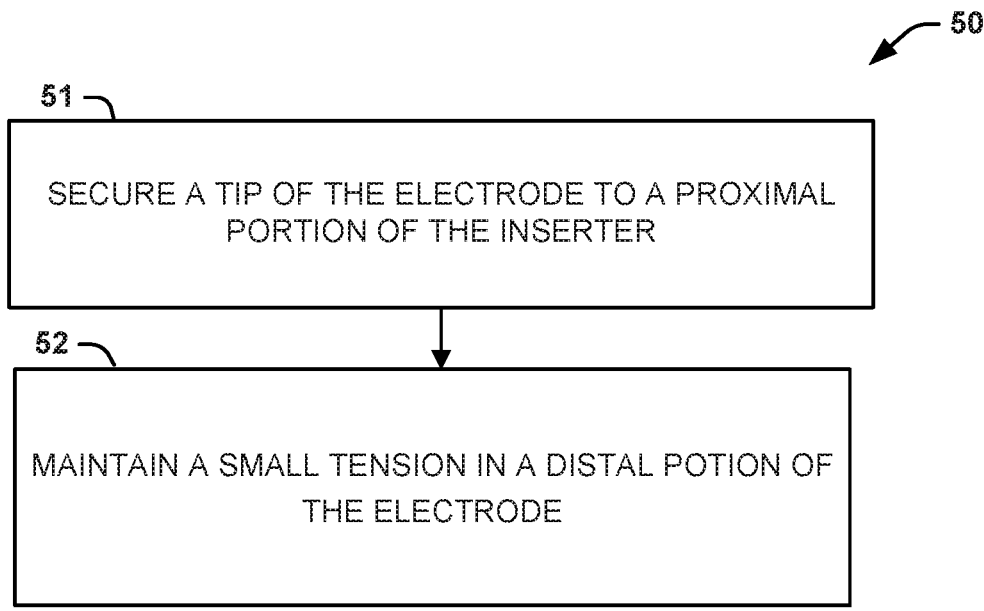
FIG. 5 is a process flow diagram of an example method for positioning an electrode on an inserter, which can be used in the method of FIG. 2.

FIG. 5 illustrates an example method 50 for positioning the electrode 11 on the inserter 12. At 51, a tip of the electrode 11 can be secured to a proximal portion of the inserter 12. In some instances, the electrode 11 can be secured by a selective release mechanism 13 that can enable the electrode 11 to be temporarily attached to the inserter 12 (e.g., so that the electrode is attached during implantation into a fascicle of a peripheral nerve or into a portion of the central nervous system, but released after implantation). In some examples, the selective release mechanism 13 can include one or more biocompatible and biodegradable elements (e.g., including a type of sugar, like sucrose). However, the selective release mechanism 13 is not limited to being biodegradable and can, instead, release based on tactile, chemical, mechanical, electrical, and/or optical means.

At 52, a small tension can be maintained in a distal portion of the electrode 11. In other words, the electrode 11 can be coupled to the inserter 12 by the selective release mechanism 13. A small tension is applied in the proximal region of the inserter 12 to maintain the electrode 11 in place. In some instances, the tension can also be based on the electrode 11 being attached to or wrapped around a spool, frame, or other mechanism. The tension can be established so that as the electrode 11 is wound around the inserter 12 and the electrode 11 remains in place (e.g., during winding, Step 54).

Figure 6:
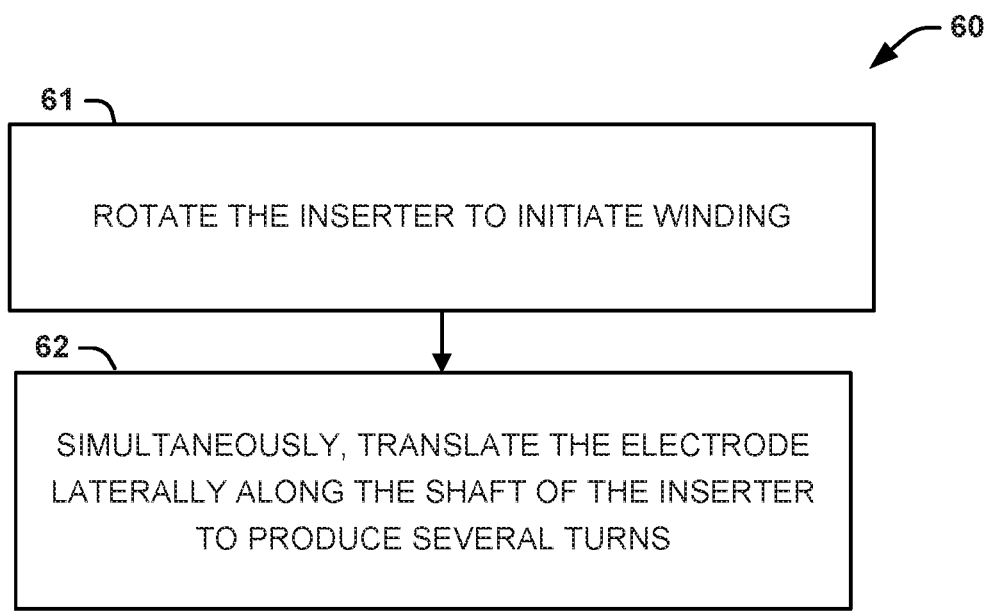
FIG. 6 is a process flow diagram of an example method for winding the electrode around the inserter, which can be used in the method of FIG. 2.

FIG. 6 illustrates an example method 50 for winding the electrode 11 around the inserter 12. At 61, the inserter 12 can be rotated to initiate the winding. For example, rotational motor 23 can cause the inserter 12 to be rotated. Simultaneously, at 62, the electrode 11 can be translated along the shaft of the inserter 12 to produce several turns or coils. For example, linear motor 24 can accomplish the translation of the electrode 11. The rotation and translation can work together to produce at least two turns or coils in the electrode 11 around the inserter 12.

Figure 7:
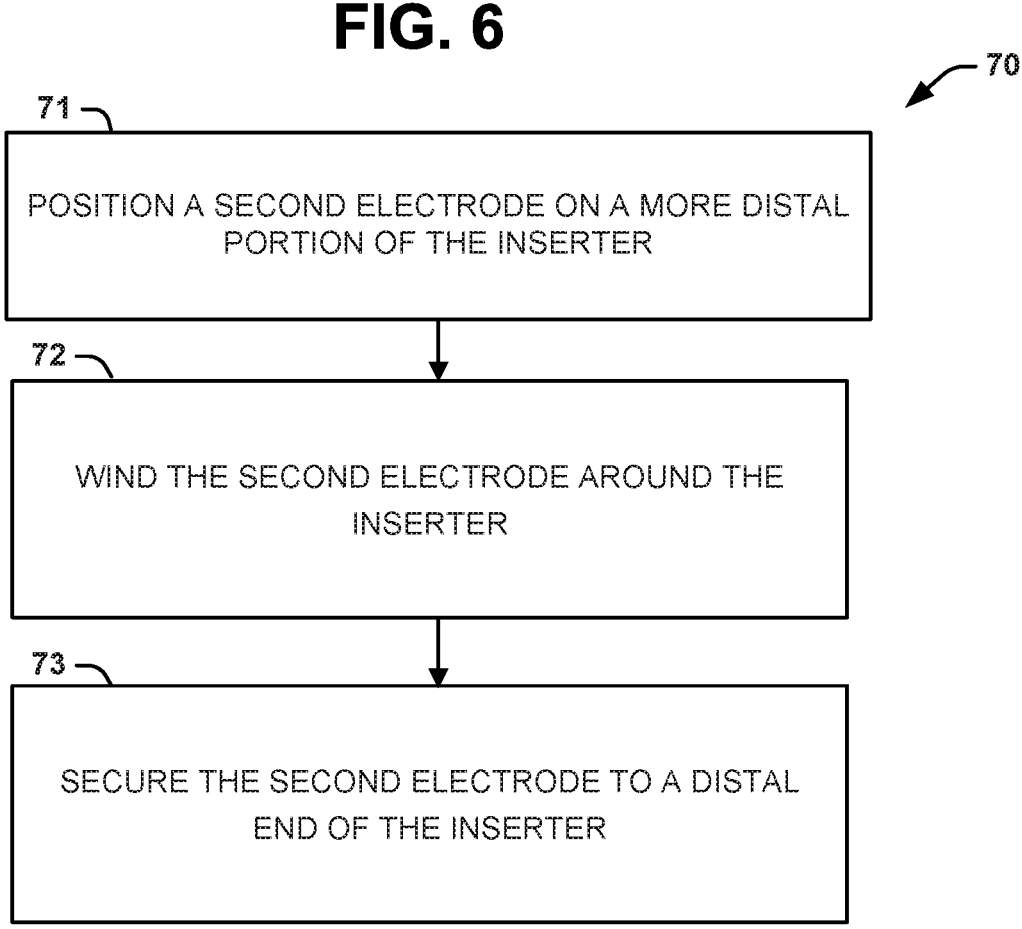
FIG. 7 is a process flow diagram of an example method for winding another electrode around the inserter, which can be used in the method of FIG. 2.

FIG. 7 illustrates an example method 70 for winding a second electrode (not shown) around the inserter 12 to create a multiple channel interface. At 71, the second electrode can be positioned on the inserter 12. For example, the second electrode can be positioned more distal than the electrode 11. A tip of the second electrode can be secured to the inserter 12 using a similar method to method 70. At 72, the second electrode can be wound around the same inserter 12 simultaneously with the electrode 11. For example, the second electrode can be wound by at least one additional motor for translation of the second electrode along the inserter 12. At 73, the second electrode can be secured to a distal end of the inserter 12. For example, the second electrode and the electrode 11 can be secured to the inserter 12. For example, the second electrode and the electrode 11 can use the same securing mechanism 14.

Alternatively, multiple electrodes can be wound around tips of an array using the example shown in FIG. 3. In this example, one or more electrodes can be wound around each tip. Multiple electrodes can be wound around the same tip using a method similar to method 70, but adjusted for the embodiment shown in FIG. 3 in which a wrapping tool 34 is used to wind each electrode 38 *a-c* around the respective tip 32 *a-c*.

From the above description, those skilled in the art will perceive improvements, changes and modifications. Such improvements, changes and modifications are within the skill of one in the art and are intended to be covered by the appended claims.

The following is claimed:

1. A method comprising:
    positioning an electrode in contact with an inserter, wherein the inserter is an elongated cylindrical shape including:
       a proximal portion comprises a sharp tip configured to facilitate entrance of the inserter into tissue, and
       a distal portion;
    securing a tip of the electrode to the proximal portion of the inserter by a selective release mechanism, wherein the electrode comprises a conductor substantially encased by an insulator;
    applying a tension to the electrode by an electrode holder;
    winding the electrode around the proximal portion of the inserter by:
       rotating the inserter to initiate the winding by a rotational motor, and
       translating the electrode distally along the length of the inserter to produce at least two coils by a linear motor, wherein the tension is maintained during the winding to keep the electrode in place; and
    securing a portion of the electrode to a distal portion of the inserter.

2. The method of claim 1, wherein winding the electrode around the proximal portion of the inserter further comprises unwinding the electrode from a spool, wherein the distal end of the electrode is attached to a spool during the winding.

3. The method of claim 1, wherein the sharp tip comprises a needle.

4. The method of claim 1, further comprising releasing tension in the electrode after the portion of the electrode is secured to the distal portion of the inserter.

5. The method of claim 1, wherein securing the distal portion of the electrode to the distal portion of the inserter further comprises securing the distal portion of the electrode to the distal portion of the inserter with an adhesive material or adhesive tape.

6. The method of claim 1, wherein the conductor comprises a wire with a lateral size of 100 µm or less.

7. The method of claim 1, wherein securing the distal portion of the electrode to the distal portion of the inserter further comprises securing the distal portion of the electrode to the distal portion of the inserter with a knot.

8. The method of claim 1, wherein securing the tip of the electrode to the proximal portion of the inserter further comprises securing the tip of the electrode to the proximal portion of the inserter with a biodegradable substance.

9. The method of claim 8, wherein the biodegradable substance comprises sucrose.

10. The method of claim 1 further comprising:
   securing a tip of a second electrode to a distal portion of the proximal portion of the inserter by a second selective release mechanism;
   applying a tension to the second electrode by the second electrode holder;
   winding the second electrode around the inserter, wherein the tension is maintained during the winding to keep the second electrode in place during the winding by a second rotational motor and a second linear motor; and
   securing a distal portion of the second electrode to a distal portion of the inserter by a holding mechanism.

11. The method of claim 10, wherein winding the second electrode around the inserter further comprises winding the second electrode around the inserter at substantially the same time as winding the electrode around the inserter.

12. The method of claim 10, wherein securing the distal portion of the second electrode to the distal portion of the inserter further comprises securing the second electrode to a same part of the distal portion of the inserter as the electrode, wherein both the electrode and the second electrode are both secured with at least one of adhesive tape or knots.

* * * * *